United States Patent
Kim et al.

(10) Patent No.: US 11,110,145 B2
(45) Date of Patent: Sep. 7, 2021

(54) COMPOSITION FOR PROTECTING CELL FROM OXIDATIVE STRESS COMPRISING GREEN TEA EXTRACT WHICH HAS MODIFIED AMOUNTS OF INGREDIENTS

(71) Applicant: AMOREPACIFIC CORPORATION, Seoul (KR)

(72) Inventors: Hyungsu Kim, Yongin-si (KR); Ayoung Kim, Yongin-si (KR); Juewon Kim, Yongin-si (KR); Si Young Cho, Yongin-si (KR); Yong-Deog Hong, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 199 days.

(21) Appl. No.: 16/110,371

(22) Filed: Aug. 23, 2018

(65) Prior Publication Data
US 2019/0091276 A1    Mar. 28, 2019

(30) Foreign Application Priority Data

Sep. 25, 2017 (KR) .......... 10-2017-0123174
Jun. 11, 2018 (KR) .......... 10-2018-0066822

(51) Int. Cl.
| A61K 36/82 | (2006.01) |
| A61K 36/00 | (2006.01) |
| A61P 39/06 | (2006.01) |
| A61K 31/353 | (2006.01) |

(52) U.S. Cl.
CPC ............ *A61K 36/82* (2013.01); *A61K 31/353* (2013.01); *A61P 39/06* (2018.01); *A61K 2236/33* (2013.01)

(58) Field of Classification Search
None
See application file for complete search history.

(56) References Cited

U.S. PATENT DOCUMENTS

| 2014/0271944 A1 | 9/2014 | Mccord et al. |
| 2017/0246235 A1* | 8/2017 | Duffield ............. A61K 31/353 |
| 2018/0000774 A1* | 1/2018 | Araldi ................ A61P 25/28 |

FOREIGN PATENT DOCUMENTS

| CN | 1346642 A | 5/2002 |
| CN | 102300578 A | 12/2011 |
| CN | 103145679 A | 6/2013 |
| CN | 103948584 A | 7/2014 |
| CN | 103988950 A | 8/2014 |
| CN | 104740089 A | 7/2015 |
| CN | 104784197 A | * 7/2015 |
| CN | 104784197 A | 7/2015 |
| CN | 104920701 A | 9/2015 |
| CN | 104970371 A | 10/2015 |
| CN | 106751926 A | 5/2017 |
| KR | 1020110023437 A | 3/2011 |
| WO | 2010065567 A2 | 6/2010 |

OTHER PUBLICATIONS

Chemistry of Life, Biochemistry and Medicine, 2007, vol. 27, No. 5, pp. 434-436; partial translation in Chinese Office Action.
Chinese Office Action dated May 26, 2021 of CN Application No. 201811120074.3.
Duan Wei-song et al., "Primary astrocytes with mutant SODIG93A are susceptible to oxidative stress," Basic & Clinical Medicine, 2010, vol. 30, No. 4, pp. 378-382; English Abstract.
Feng Li-qin et al., "Antioxidant activities of tea polyphenols from selenium enriched tea," Food Science and Technology, 2016, vol. 41, No. 12, pp. 154-157; English Abstract.
Fengjun Deng et al., "Neuroprotective effect of epigallocatechin-3-gallate on hemisection-induced spinal cord injury in ratstrade," Neural Regeneration Research, 2011, Vo. 6, No. 6, pp. 405-411.
Liang Gang et al., "Antioxidative effect of three components of catechin isolated from green tea," Journal of Guangxi Medical University, 1998, vol. 15, No. 1, pp. 7-9; English Abstract.
Liu Da-mai et al., "Progress in Antioxidant Effects of Tea Polyphenols in Vivo," Shandong Medicine, 2013, vol. 53, No. 16, pp. 82-84; partial translation in Chinese Office Action.
Liu Ting-ting et al., "Research progress on anti-oxidative mechanism of epigallocatechin gallate," Drugs & Clinic, 2016, Vo. 31, No. 6, pp. 919-923; English Abstract.

* cited by examiner

*Primary Examiner* — Michael Barker
*Assistant Examiner* — Randall O Winston
(74) *Attorney, Agent, or Firm* — Cantor Colburn LLP

(57) ABSTRACT

Disclosed is to provide a composition which is derived from a natural product and exhibits an excellent effect of protecting cells from oxidative stress and a method for preparing the same. The extract and composition according to one aspect of the present disclosure are derived from a natural product, thus are safe. It can prevent, ameliorate and treat oxidative stress and neuron damage. Therefore, it allows to improve the quality of life of the elderly population without concerns about side effects and promote development of the related industry.

8 Claims, 6 Drawing Sheets

COMPOSITION FOR PROTECTING CELL FROM OXIDATIVE STRESS COMPRISING GREEN TEA EXTRACT WHICH HAS MODIFIED AMOUNTS OF INGREDIENTS

CROSS-REFERENCE TO RELATED APPLICATION

This application claims the priority of Korean Patent Application No. 10-2017-0123174, filed on Sep. 25, 2017 and Korean Patent Application No. 10-2018-0066822, filed on Jun. 11, 2018 and all the benefits accruing therefrom under 35 U.S.C. § 119, the contents of which in its entirety are herein incorporated by reference.

BACKGROUND

1. Field

The present disclosure relates to a composition for protecting cells from oxidative stress comprising a green tea extract which has modified amounts of ingredients.

2. Description of the Related Art

Oxidation means that certain atoms, molecules, and ions lose the electrons or certain substances bond with oxygen or lose hydrogen. The phenomena that certain substances burn, certain substances rust, alcohols convert to aldehydes, oil acidifies, and apples are browned are all redox reactions. These phenomena occur even when certain substances are placed in the air, and it can be said that such an oxidation reaction results from oxygen.

Such an oxidation reaction takes place in cells as well, and for example, an oxidation reaction by active oxygen which exhibits a strong oxidizing power may be mentioned. Active oxygen is also called noxious oxygen and is oxygen in an unstable state to be completely different from oxygen we breathe in. Active oxygen is overproduced by environmental pollution, chemicals, ultraviolet rays, blood circulation disorder, stress and the like. This overproduced active oxygen causes oxidation in the human body. This will damage the cell membrane, DNA, and all other cell structures, and the cells lose the function or are altered depending on the extent of the damage. Along with this, various amino acids in the body are oxidized and the function of protein deteriorates. Moreover, active oxygen damages nucleic acid to cause the deformation and isolation of nucleic acid base, cleavage of bond, and oxidative decomposition of saccharide, and the like, which may cause mutation or cancer. In addition, the physiological function deteriorates, and this causes various diseases and aging.

In particular, the onset of degenerative cranial nerve system diseases caused by oxidative stress is also increasing as the aging population rapidly increases, and it is the actual situation that prevention and treatment methods for degenerative cranial nerve system diseases are still unclear and a drug having a decisive effect has not been found out despite the remarkable development in medical science. Currently, researches on the therapeutic agents and treatment methods for degenerative cranial nerve system diseases have been continuously conducted, but side effects and toxicity due to long-term use of certain drugs are often a problem and most therapeutic agents only exhibit the effect of alleviating the symptoms rather than the fundamental treatment. It is thus imperative to develop a therapeutic agent which is derived from a natural product and can fundamentally treat degenerative cranial nerve system diseases without any side effects and toxicity.

SUMMARY

The present disclosure is intended to provide a composition which is derived from a natural product, does not exhibit toxicity, and exhibits an excellent effect of protecting cells, and a method for preparing the same.

In order to solve the above problems, in one aspect, the present disclosure provides a composition for protecting cells from oxidative stress comprising as an active ingredient a green tea extract containing (−)-gallocatechin gallate (GCG) at 5 to 25% by weight based on a total weight of the composition and (−)-epigallocatechin gallate (EGCG) at 7 to 15% by weight based on a total weight of the composition.

In another aspect, the present disclosure provides a method for protecting cells from oxidative stress, comprising administering a composition comprising as an active ingredient a green tea extract containing (−)-gallocatechin gallate (GCG) at 5 to 25% by weight based on a total weight of the composition and (−)-epigallocatechin gallate (EGCG) at 7 to 15% by weight based on a total weight of the composition to a subject in need thereof.

In another aspect, the present disclosure provides a composition for prevention or amelioration of a neurodegenerative disease comprising the green tea extract as an active ingredient. In an aspect, the neurodegenerative disease may be caused by neuron damage due to oxidative stress.

In another aspect, the present disclosure provides a method for prevention or amelioration of a neurodegenerative disease, comprising administering a composition comprising the green tea extract as an active ingredient.

In another aspect, the present disclosure provides a method for preparing the composition, comprising the steps of: (1) adding ethanol to green tea and performing extraction at 50 to 70° C. for 30 minutes to 4 hours; (2) removing ethanol by filtration and decompression; and (3) adding water, stirring the mixture at 70 to 100° C. for 3 to 8 hours and then concentrating it under reduced pressure.

DETAILED DESCRIPTION

Figure 1:
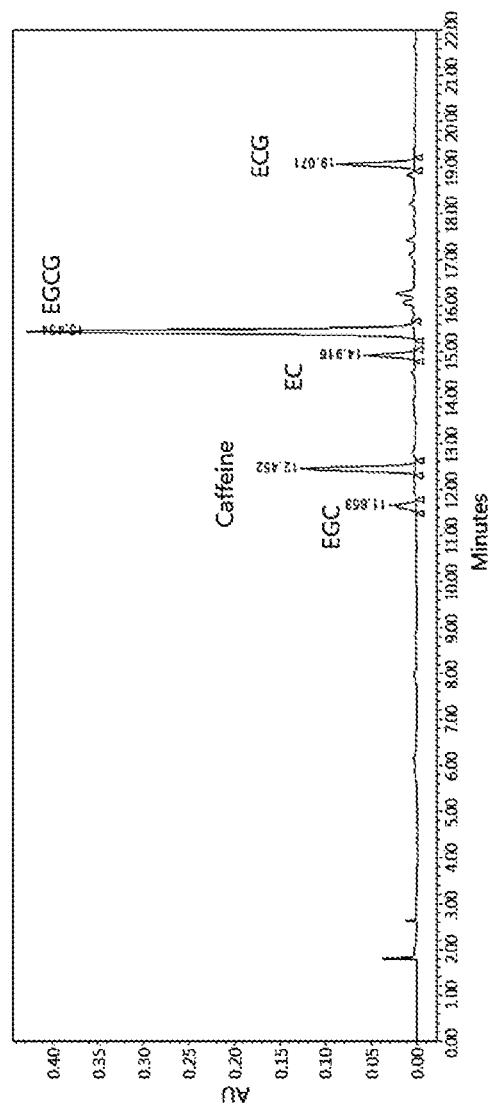
FIG. 1 is a chromatogram of the green tea extract notified by the Korean Ministry of Food and Drug Safety of Example 1 (Sample 1)

As used herein, the term "green tea extract" covers an extract of *Camellia sinensis*, an evergreen tree belonging to the family Theaceae, or an extract from tea leaves treated with *Bacillus subtilis* spp. and then fermented, etc., regardless of the extraction method, extraction solvent, and the form of the extracted ingredient or of the extract. It also covers fractions obtained by fractionating the extracts with a specific solvent. The tea includes at least one selected from the group consisting of tea leaves, flowers, stems, fruits, roots, and the cores of stems and roots. The tea may preferably be tea leaves. In addition, the extract may preferably be in powder form. The extraction or fractionation may be performed using water, an organic solvent, or a mixed solvent thereof. The organic solvent may be an alcohol, isopropanol, acetone, hexane, ethyl acetate, carbon dioxide, or a mixed solvent of two or more of them, although not limited thereto. The extraction or fractionation may be performed at room temperature or elevated temperature under conditions where the active ingredient of green tea is not destroyed or where the destruction is minimized. The alcohol may be a C1 to C5 lower alcohol. The number and method of the extraction or the fractionation is not particularly limited. For example, methods such as cold extraction, ultrasonic extraction, reflux cooling extraction, hot water extraction may be used. Preferably, the green tea extract of the present disclosure may be obtained by extracting or fractionating the active ingredient by cold or hot extraction, filtering the extract, and concentrating the filtrate under reduced pressure.

As used herein, the term "oxidative stress" refers to side effects of noxious oxygen. The human body regulates the amount of active oxygen in the body itself, but various diseases caused by noxious oxygen are induced when the production of noxious oxygen suddenly increases by various situations or the function of removing noxious oxygen decreases. The side effects of noxious oxygen accordingly caused are called oxidative stress. The cell's genes are affected or damaged when active oxygen is overproduced and oxidative stress continuously accumulates in the body. For example, the active oxygen species overproduced by $H_2O_2$ has a free radical and is in an unstabilized state, and thus it exhibits strong activity. Consequently, the active oxygen species oxidizes proteins, lipids, and the like in cells so as to destroy the homeostasis of the cells and kill the cells. In particular, such oxidative stress with respect to neurons causes neurodegenerative diseases and the like.

As used herein, the term "epicatechin" covers epigallocatechin (EGC), (−) epicatechin (EC), (−)-epigallocatechin gallate (EGCG), and epicatechin 3-O-gallate (ECG).

In an aspect, the present disclosure may relate to a composition for protecting cells from oxidative stress comprising as an active ingredient a green tea extract containing (−)-gallocatechin gallate (GCG) at 5 to 25% by weight based on a total weight of the composition or the extract and (−)-epigallocatechin gallate (EGCG) at 7 to 15% by weight based on the total weight of the composition or the extract.

In an aspect of the present disclosure, the composition may be a composition for treatment, prevention or amelioration of a disease caused by neuron death.

In another aspect, the present disclosure may be a composition for prevention or amelioration of a neurodegenerative disease, which contains the green tea extract as an active ingredient.

In one aspect, the content of the GCG may be 5% by weight or more, 6% by weight or more, 7% by weight or more, 8% by weight or more, 9% by weight or more, 10% by weight or more, 11% by weight or more, 12% by weight or more, 12.52% by weight or more, 13% by weight or more, 14% by weight or more, 16% by weight or more, 18% by weight or more, 20% by weight or more, 22% by weight or more or 24% by weight or more, based on the total weight of the composition or the extract. In another aspect, the content of the GCG may be 25% by weight or less, 23% by weight or less, 21% by weight or less, 19% by weight or less, 17% by weight or less, 15% by weight or less, 14% by weight or less, 13% by weight or less, 12.55% by weight or less, 12% by weight or less, 11% by weight or less, 10% by weight or less, 9% by weight or less, 8% by weight or less, 7% by weight or more or 6% by weight or less, based on the total weight of the composition or the extract.

In one aspect, the content of the EGCG may be 7% by weight or more, 8% by weight or more, 8.48% by weight or more, 8.5% by weight or more, 9% by weight or more, 10% by weight or more, 12% by weight or more, or 14% by weight or more, based on the total weight of the composition or the extract. In another aspect, the content of the EGCG may be 15% by weight or less, 13% by weight or less, 11% by weight or less, 10% by weight or less, 9% by weight or less, 8.5% by weight or less, 8.48% by weight or less, 8.3% by weight or less, 8% by weight or less, or 7.5% by weight or less, based on the total weight of the composition or the extract.

In another embodiment, the total content of the GCG and the EGCG in the extract may be 40% by weight or less based on the total weight of the composition or the extract. In one aspect, the content of the catechin may be 40% by weight or less, 35% by weight or less, 30% by weight or less, 25% by weight or less, 20% by weight or less, 18% by weight or less, 16% by weight or less, 15% by weight or less, 14% by weight or less, 12% by weight or less, 10% by weight or less, 8% by weight or less, 6% by weight or less, or 4% by weight or less, based on the total weight of the composition or the extract. In another aspect, the total content of the GCG and the EGCG may be 3% by weight or more, 6% by weight or more, 8% by weight or more, 10% by weight or more, 12% by weight or more, 13% by weight or more, 14% by weight or more, 16% by weight or more, 18% by weight or more, 20% by weight or more, 25% by weight or more, 30% by weight or more, or 35% by weight or more, based on the total weight of the composition or the extract.

In another embodiment, the content of the epicatechin in the extract may be 20% by weight or less, based on the total weight of the composition or the extract. In one aspect, the content of the epicatechin may be 20% by weight or less, 18% by weight or less, 16% by weight or less, 15% by weight or less, 14% by weight or less, 12% by weight or less, 10% by weight or less, 8% by weight or less, 6% by weight or less, or 4% by weight or less, based on the total weight of the composition or the extract. In another aspect, the content of the catechin may be 3% by weight or more, 6% by weight or more, 8% by weight or more, 10% by weight or more, 12% by weight or more, 13% by weight or more, 14% by weight or more, 16% by weight or more, or 18% by weight or more, based on the total weight of the composition or the extract.

In another embodiment, the extract may be an extract obtained by at least one extraction with at least one selected from the group consisting of water and $C_1$ to $C_4$ alcohols. In one aspect, the alcohol may be ethanol. In another aspect, the alcohol may be at least 20%, at least 30%, at least 40%, at least 50%, at least 60% or at least 70% ethanol. In another aspect, the alcohol may be up to 70%, up to 60%, up to 50%, up to 40%, or up to 30% ethanol.

In another embodiment, the content of the extract in the composition may be 1 to 100% by weight on a dry weight basis. In one aspect, the content of the extract in the composition may be 1% by weight or more, 10% by weight or more, 20% by weight or more, 30% by weight or more, 40% by weight or more, 50% by weight or more, 60% by weight or more, 70% by weight or more, 80% by weight or more, or 90% by weight or more on a dry weight basis. In another aspect, the content of the extract in the composition may be 100% by weight or less, 90% by weight or less, 80% by weight or less, 70% by weight or less, 60% by weight or less, 50% by weight or less, 40% by weight or less, 30% by weight or less, or 20% by weight or less on a dry weight basis.

In another embodiment, the dose of the active ingredient may be 5 mg/kg/day to 1000 mg/kg/day on a dry weight basis. In one aspect, the dose may be 5 mg/kg/or more, 100 mg/kg/or more, 200 mg/kg/or more, 300 mg/kg/or more, 400 mg/kg/or more, 500 mg/kg/or more, 600 mg/kg/or more, 700 mg/kg/or more, 800 mg/kg/or more, or 900 mg/kg/or more. In another aspect, the dose may be 1000 mg/kg/or less, 900 mg/kg/or less, 800 mg/kg/or less, 700 mg/kg/or less, 600 mg/kg/or less, 500 mg/kg/or less, 400 mg/kg/or less, 300 mg/kg/or less, 200 mg/kg/or less, 100 mg/kg/or less, 50 mg/kg/or less, or 10 mg/kg/or less.

In one embodiment, the oxidative stress may result from active oxygen species. The active oxygen species refers to a state in which the active oxygen species has a free radical and is not stabilized, and thus it exhibits strong activity. The active oxygen species is sometimes called noxious oxygen since overproduction thereof exhibits toxicity to the living body, that is, causes oxidative stress. The active oxygen species destroys the homeostasis of cells by oxidizing huge molecules (proteins, lipids, and the like) in the cells, kills the cells, and thus causes catastrophic damage to the cell tissue. Active oxygen species includes singlet oxygen, a superoxide radical, a hydroxy radical, and hydrogen peroxide ($H_2O_2$). In other words, the active oxygen species is increased by $H_2O_2$, and accordingly the oxidative stress increases. In one aspect, the present disclosure exhibits an excellent effect of protecting cells from active oxygen species, also excellent DPPH (diphenyl-2-picrylhydrazyl) radical scavenging ability, and thus can effectively protect cells from oxidative stress.

In another embodiment, the oxidative stress may be caused by brain tissue lipid peroxidation.

In still another embodiment, the oxidative stress may result from the peroxidation product malondialdehyde.

In yet another embodiment, the cell may be a brain cell or a neuron.

In one aspect of the present disclosure, the composition may be a composition for treatment, prevention or amelioration of a disease caused by neuron death.

In another aspect, the present disclosure may be a composition for prevention or amelioration of a neurodegenerative disease, which contains the green tea extract as an active ingredient.

The neuron death due to oxidative stress is known to be a main cause of degenerative cranial nerve system diseases. Recently, oxidative stress due to a rapid increase in the amount of active oxygen species in neurons is considered as the main cause of the occurrence of the degenerative cranial nerve system diseases including stroke, amyotrophic lateral sclerosis (Lou Gehrig's disease), Parkinson's disease, Huntington's disease, spinal cord cerebellar degeneration and multiple sclerosis. Hence, it has been reported that such diseases can be prevented or treated by inhibiting or decreasing oxidative stress. In one aspect, the present disclosure can decrease oxidative stress caused by active oxygen species and thus can protect neurons and suppress the death thereof.

In addition, lipid peroxidation refers to conversion of a lipid into a lipid peroxide. The fatty acid part of a lipid is peroxidized. Lipid peroxidation products include lipids having a hydroperoxyl group, lipids having an internally peroxidized structure, lipids having a hydroperoxyl radical, and in some cases, degradation products thereof. In general, the hydroperoxyl group is unstable and frequently generate radicals. It is believed that induction of a chain reaction of these radicals is a cause of tissue damage in organisms. In other words, lipofuscin, which appears in the nerves, liver, myocytes, etc. of aged animals, is thought to be an insoluble inhomogeneous polymer in which proteins, etc. are swept around lipid peroxides. Peroxidation of the membrane lipids changes the properties of the membrane such as permeability. Also, it is harmful to a living body as it is considered as a factor implicated in vascular lesion. Hydroperoxyl cholesterol is also known. Given its chemical structure, it can be considered as an alcohol peroxide. It is known to be clinically associated with aging. In particular, lipid peroxide is known to be a cause of brain aging. Thus, lipid peroxide leads to brain aging, cranial nerve diseases, particularly neurodegenerative diseases. Therefore, it is possible to ameliorate neurodegenerative diseases by reducing lipid peroxides. In one aspect, the present disclosure allows to decrease lipid peroxidation products in the brain tissues, thereby preventing and ameliorating neurodegenerative diseases.

In an aspect, the neurodegenerative disease may be one or more selected from the group consisting of stroke, amyotrophic lateral sclerosis (Lou Gehrig's disease), Parkinson's disease, Huntington's disease, spinal cord cerebellar degeneration, and multiple sclerosis.

In another aspect, the composition may be a food composition or a pharmaceutical composition.

The formulation of the food composition is not particularly limited. However, the composition may be formulated into, for example, tablets, granules, pills, powders, liquids such as drinks, caramels, gels, bars, tea bags, etc. Each formulation may include an ingredient commonly used in the corresponding field in addition to the active ingredient. The ingredient may be selected and mixed by those skilled in the art without difficulty depending on the formulation or use and may provide a synergistic effect when applied with the other raw materials. Also, the food may be a health functional food.

The composition may be administered by various methods such as intake, drinking, injection, spraying or squeezing.

The determination of the dose of the active ingredient of the food composition according to one aspect of the present disclosure is within the knowledge of those skilled in the art. The dose may vary depending on various factors including the age, health condition, and complications of the subject.

The food composition according to one aspect of the present disclosure may be, for example, various foods such as chewing gums, caramel products, candies, frozen desserts, and confectionery, beverage products such as soft drinks, mineral water, and alcoholic beverages, and health functional foods including vitamins and minerals.

In addition to the above ingredients, the food composition according to one aspect of the present disclosure may comprise various nutrients, a vitamin, a mineral (electrolyte), flavoring agents such as a synthetic flavoring agent and a natural flavoring agent, a colorant and an improving agent (cheese, chocolate, etc.), pectic acid or a salt thereof, alginic acid or a salt thereof, an organic acid, a protective colloidal thickening agent, a pH adjuster, a stabilizer, a preservative, glycerin, an alcohol, a carbonating agent as used in carbonated beverages, etc. Besides, the food compositions according to one aspect of the present disclosure may comprise fruit flesh for the production of natural fruit juices, fruit beverages and vegetable beverages. These ingredients may be used alone or as a mixture thereof. The content of these additives is not so critical. However, generally it is 0 to about 60 parts by weight based on 100 parts by weight of the composition according to one aspect of the present disclosure.

The pharmaceutical composition according to one aspect of the present disclosure may be administered orally, parenterally, rectally, topically, transdermally, intravenously, intramuscularly, intraperitoneally, subcutaneously, etc. The formulation for oral administration may be a tablet, a pill, a hard or soft capsule, a granule, a powder, a fine granule, a liquid, an emulsion, or a pellet, although not limited thereto. The formulation for parenteral administration may be a solution, a suspension, an emulsion, a gel, an injection, a drop, a suppository, a patch, or a spray, although not limited thereto. The formulations can be easily prepared according to methods commonly employed in the art and may further comprise a surfactant, an excipient, a hydrating agent, an emulsifying accelerator, a suspending agent, a salt or buffer for controlling osmotic pressure, a colorant, flavoring, a stabilizer, a preservative, or other commonly used adjuvants.

The composition according to one aspect of the present disclosure may comprise a pharmaceutically acceptable salt, and the salt may comprise (1) an acid addition salt formed with an inorganic acid such as hydrochloric acid, hydrobromic acid, sulfuric acid, nitric acid, and phosphoric acid; or with an organic acid such as acetic acid, propionic acid, hexanoic acid, cyclopentane propionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo [2,2,2]-oct-2-en-1-carboxylic acid, glucoheptonic acid, 3-phenylpropionic acid, trimethylacetic acid, tert-butylacetic acid, lauryl sulfuric acid, gluconic acid, glutamic acid, hydroxynaphthoic acid, salicylic acid, stearic acid, and muconic acid; or (2) a salt formed when an acidic proton present in the parent compound is substituted.

The dose of the pharmaceutical composition according to one aspect of the present disclosure will vary depending on the age, gender, body weight, pathological condition and severity of the subject, route of administration, and judgment of the prescriber. The determination of the dose of the active ingredient based on these factors is within the knowledge of those skilled in the art.

In another aspect, the present disclosure may relate to a method for preparing the composition, comprising the steps of: (1) adding ethanol to green tea and performing extraction at 50 to 70° C. for 30 minutes to 4 hours; (2) removing ethanol by filtration and decompression; and (3) adding water, stirring the mixture at 70 to 100° C. for 3 to 8 hours and then concentrating it under reduced pressure.

In one aspect, the ethanol may be at least 20%, at least 30%, at least 40%, at least 50%, at least 60%, or at least 70% ethanol. In another aspect, the ethanol may be up to 70%, up to 60%, up to 50%, up to 40%, or up to 30% ethanol.

In one aspect, the temperature of step (1) may be 50° C. or higher, 55° C. or higher, 60° C. or higher, 65° C. or higher, or 68° C. or higher. In another aspect, the temperature of step (1) may be 70° C. or lower, 65° C. or lower, 60° C. or lower, 55° C. or lower, or 52° C. or lower.

In one aspect, the time of step (1) may be 30 minutes or more, 40 minutes or more, 50 minutes or more, 60 minutes or more, 70 minutes or more, 80 minutes or more, 90 minutes or more, 100 minutes or more, 120 minutes or more, 140 minutes or more, 160 minutes or more, 180 minutes or more, 200 minutes or more, or 220 minutes or more. In another aspect, the time of step (1) may be 240 minutes or less, 220 minutes or less, 200 minutes or less, 180 minutes or less, 160 minutes or less, 140 minutes or less, 120 minutes or less, 100 minutes or less, 90 minutes or less, 80 minutes or less, 70 minutes or less, 60 minutes or less, 50 minutes or less, or 40 minutes or less.

In one aspect, the temperature of step (3) may be 70° C. or higher, 75° C. or higher, 80° C. or higher, 90° C. or higher, 95° C. or higher, or 98° C. or higher. In another aspect, the temperature of step (3) may be 100° C. or lower, 95° C. or lower, 90° C. or lower, 85° C. or lower, 80° C. or lower, or 75° C. or lower.

In one aspect, the stirring time of step (3) may be 30 minutes or more, 1 hour or more, 2 hours or more, 3 hours or more, 4 hours or more, 5 hours or more, 6 hours or more, or 7 hours or more. In another aspect, the stirring time of step (3) may be 8 hours or less, 7 hours or less, 6 hours or less, 5 hours or less, 4 hours or less, 3 hours or less, 2 hours or less, or 1 hour or less.

In another embodiment, the weight ratio of the product of step (2) and the water added in step (3) may be 1:7 to 1:12. In one aspect, the weight ratio may be 1:5 or more, 1:6 or more, 1:7 or more, 1:8 or more, 1:9 or more, 1:10 or more, 1:12 or more, 1:14 or more, 1:16 or more, or 1:18 or more. In another aspect, the weight ratio may be 1:20 or less, 1:18 or less, 1:16 or less, 1:14 or less, 1:12 or less, 1:11 or less, 1:10 or less, 1:9 or less, 1:8 or less, 1:7 or less, or 1:6 or less.

In another embodiment, the yield of the product after step (3) may be 5 to 30% by weight based on the weight of the green tea in step (1). In one aspect, the yield may be 5% by weight or more, 6% by weight or more, 8% by weight or more, 10% by weight or more, 12% by weight or more, 14% by weight or more, 16% by weight or more, 18% by weight or more, 20% by weight or more, 22% by weight or more, 24% by weight or more, 26% by weight or more, or 28% by weight or more. In another aspect, the yield may be 30% by weight or less, 28% by weight or less, 26% by weight or less, 24% by weight or less, 22% by weight or less, 20% by weight or less, 18% by weight or less, 16% by weight or less, 14% by weight or less, 12% by weight or less, 10% by weight or less, 8% by weight or more, or 6% by weight or less.

Hereinafter, the constitution and effects of the present disclosure will be described in more detail through examples, test examples, and formulation examples. However, the following examples are provided for illustrative purposes only to facilitate understanding of the present disclosure, and the scope of the present disclosure are not limited thereto.

Example 1: Preparation of a Green Tea Extract Notified by the Korean Ministry of Food and Drug Safety and a High Temperature Processed Green Tea Extract 1000 ml of 50% ethanol was added to 100 g of green tea (*Camellia sinensis*, O'sulloc Farm in Jeju) and the mixture was refluxed at 60° C. for 1 hour. The temperature of the sample was lowered to room temperature, followed by filtration. The filtrate was distilled under reduced pressure to obtain 23 g of a green tea extract notified by the Korean Ministry of Food and Drug Safety (GT-LE-35CAT, Sample 1) as a dark brown powder (yield: 23%).

10 g of Sample 1 was dissolved in 90 ml of water, and the mixture was stirred at 80° C. for 30 minutes to 8 hours. Then, the temperature was lowered to room temperature and the insoluble matter was filtered. The filtrate was concentrated under reduced pressure to obtain 10 g of a high temperature processed green tea extract. At this time, the contents of GCG, etc. of the high temperature processed green tea extract obtained at each of the stirring time intervals were measured using apparatuses as shown in Table 1 below, to identify changes in the contents of GCG, etc. over time (the contents of the ingredients in the extract at each time interval are as shown in Table 4) and identify the time zone in which GCG is most abundant. Stirring was stopped at the time zone and 10 g of a high temperature processed green tea extract (GT-LE-10GCG, HTP-GTE) was obtained. The thus-obtained extract was used as Sample 2.

Also, the contents of GCG, etc. of the high temperature processed green tea extract obtained at each of the stirring time intervals were measured using apparatuses as shown in Table 5 below, to identify changes in the contents of GCG, etc. over time (the contents of the ingredients in the extract at each time interval are as shown in Table 7). Stirring was stopped when the content of GCG reached 5 to 8% and 10 g of a high temperature processed green tea extract was obtained. The thus-obtained extract was used as Sample 3.

Figure 2:
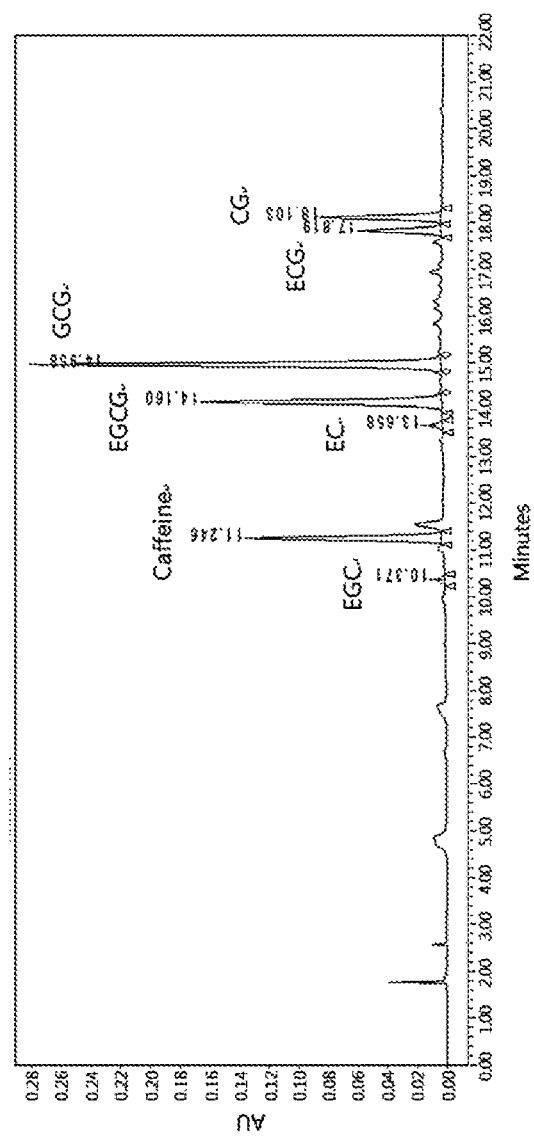
FIG. 2 is a chromatogram of a high temperature processed green tea extract according to one aspect of the present disclosure (Sample 2)

The conditions and results of the analysis of the composition of the three obtained extracts are shown in Table 1 to Table 3, Table 5 and Table 6, respectively. The chromatograms of two extracts are shown in FIG. 1 (Sample 1) and FIG. 2 (Sample 2). From the results, it was found that Sample 2 was different in composition from conventional green tea extract.

TABLE 1

Conditions of the analysis of composition

| | |
|---|---|
| Column | Sun fire C18 5 um, 4.6 × 250 mm |
| Detector | UV 280 nm |
| Apparatus | Waters 2998 PDA Detector, Waters 1525 Pump, Waters 2707 Autosampler |

TABLE 1-continued

Conditions of the analysis of composition

| | |
|---|---|
| Dilution | Gradient A: water with 0.1% TFA (trifluoroacetic acid), Gradient B: acetonitrile with 0.1% TFA |
| Gradient profile | 0 min A(95):B(5)1 min A(95):B(5) |
| | 20 min A(71):B(29) |
| | 22 min A(71):B(29) |
| Flow rate | 1 ml/min |
| Injection volume | 20 μl |

TABLE 2

| Sample 1 EGC | Caffeine | EC | EGCG | ECG | Total amount of epicatechin |
|---|---|---|---|---|---|
| 9.16 | 3.21 | 3.63 | 20.93 | 2.62 | 36.34 |

TABLE 3

| Sample 2 EGC | Caffeine | EC | EGCG | ECG | GCG | CG | Total amount of epicatechin | GCG + EGCG |
|---|---|---|---|---|---|---|---|---|
| 2.16 | 3.28 | 0.75 | 8.48 | 1.90 | 12.52 | 2.38 | 13.28 | 21 |

TABLE 4

| Stirring time | EGCG | GCG | ECG | CG |
|---|---|---|---|---|
| 1 hour | 11.79 | 7.6 | 1.16 | 1.16 |
| 3 hours | 9.67 | 11.08 | 2.44 | 1.46 |
| 5 hours | 8.48 | 12.52 | 1.9 | 2.38 |
| 7 hours | 6.71 | 9.44 | 1.85 | 1.56 |

TABLE 5

Conditions of the analysis of composition

| | |
|---|---|
| Column | Thermofisher C18 5 um, 4.6 × 250 mm |
| Detector | UV 280 nm |
| Dilution | Gradient A: water with 0.1% TFA (trifluoroacetic acid), Gradient B: acetonitrile with 0.1% TFA |
| Gradient profile | 0 min A(90):B(10)30 min A(85):B(15) |
| | 42 min A(80):B(20) |
| | 44 min A(5):B(95) |
| | 49 min A(90):B(10) |
| Flow rate | 1 ml/min |
| Injection volume | 20 μl |

TABLE 6

| Sample 3 | EGC | Caffeine | EC | EGCG | ECG | GCG | CG | Total amount of epicatechin | GCG + EGCG |
|---|---|---|---|---|---|---|---|---|---|
| | 4.56 | 4.58 | 2.27 | 10.39 | 2.79 | 7.59 | 0.87 | 20.01 | 17.98 |

TABLE 7

| Stirring time | EGCG | GCG | ECG | CG |
| --- | --- | --- | --- | --- |
| 1 hour | 16.28 | 3.09 | 3.82 | 0.84 |
| 3 hours | 13.74 | 6.08 | 3.08 | 0.85 |
| 5 hours | 11.23 | 7.21 | 2.83 | 0.86 |
| 6 hours | 10.39 | 7.59 | 2.79 | 0.87 |

(In the above Table 2 to Table 4, Table 6 and Table 7, EGC denotes epigallocatechin, EC denotes (−)epicatechin, and ECG denotes epicatechin 3-O-gallate.)

(In the above Table 2 to Table 4, Table 6 and Table 7, the unit is % by weight based on the total weight of the sample.)

Test Example 1: Neurotoxicity Test

The PC12 cell line (neurocytoma) obtained from the Korean Cell Line Bank was seeded in a 96-well plate (FALCON) at 1×105 cells per well and cultured in a 5% CO2 incubator at 37° C. for 24 hours. The cells were treated with 3, 10, 20, and 30 μg/ml of each of Sample 1 and Sample 2, and further cultured for 24 hours.

Then, the medium was removed, and then the cell viability was determined using Cell Counting Kit-8 (Dojindo). 10 μl of Cell Counting Kit-8 (Dojindo) solution was added to 100 μl of RPMI1640 (Lonza), and the mixture was applied to the cells. The number of living cells was quantified by measuring the absorbance at 450 nm. The cell count or cell viability (%) was calculated by the following equation:

Cell viability (%)=(absorbance of the sample-treated group−absorbance of the reaction reagent alone)/(absorbance of the untreated group−absorbance of the reaction reagent only)×100

Figure 3:
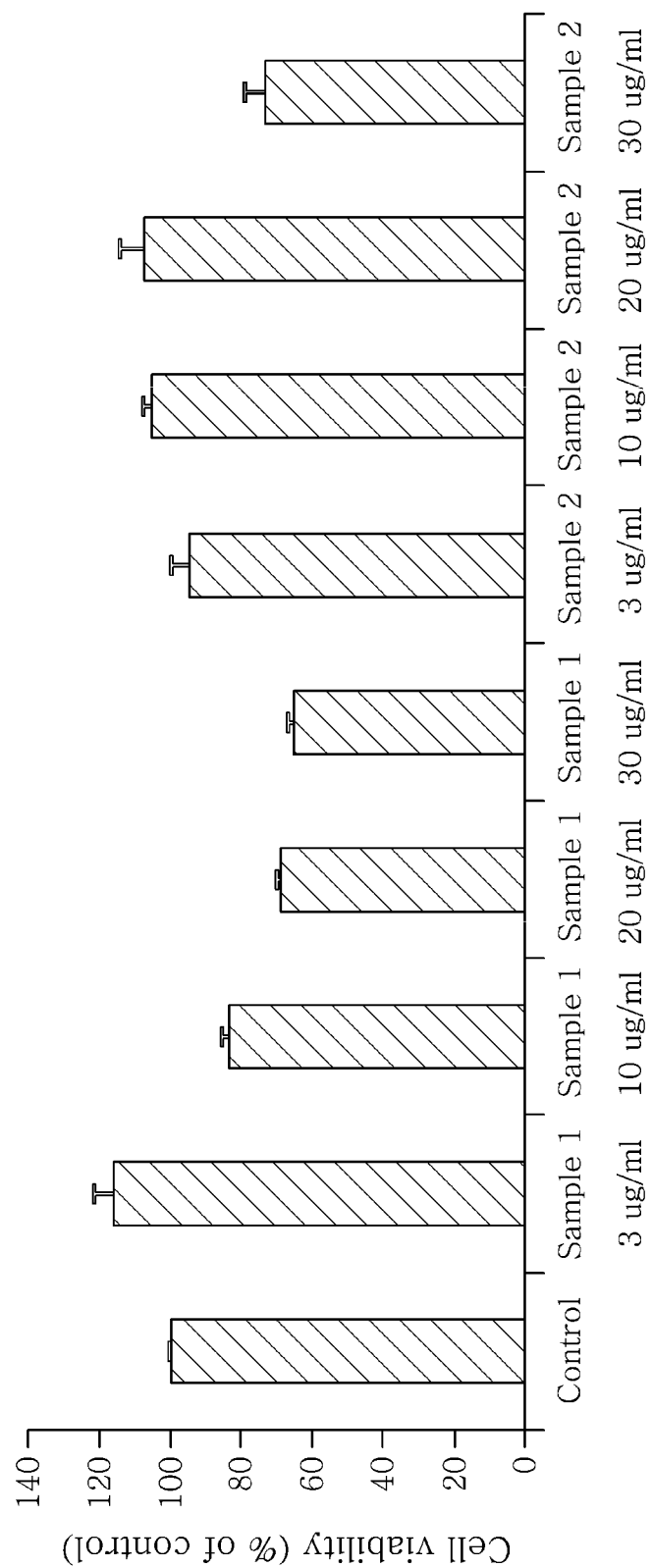
FIG. 3 shows the neurotoxicity test results of Sample 1 and Sample 2.

The results were as illustrated in FIG. 3, and Sample 2 was confirmed to be less toxic to neurons than Sample 1.

Test Example 2: Determination of Protection Against Oxidative Stress of Neurons

The PC12 cell line (neurocytoma) obtained from the Korean Cell Line Bank was seeded in a 96-well plate (FALCON) at 1×105 cells per well and cultured in a 5% CO2 incubator at 37° C. for 24 hours. The cells were treated with 3, 10, 20, and 30 μg/ml of each of Sample 1 and Sample 2, and further cultured for 24 hours. Thereafter, the cells were treated with 300 μM of $H_2O_2$ for 2 hours except the control group in order to induce oxidative stress. Then, the medium was removed, and then the cell viability was determined using Cell Counting Kit-8 (Dojindo). 10 μl of Cell Counting Kit-8 (Dojindo) solution was added to 100 μl of RPMI1640 (Lonza), and the mixture was applied to the cells. The number of living cells was quantified by measuring the absorbance at 450 nm.

Cell viability (%)=(absorbance of the sample-treated group−absorbance of the reaction reagent alone)/(absorbance of the untreated group−absorbance of the reaction reagent only)×100

Figure 4:
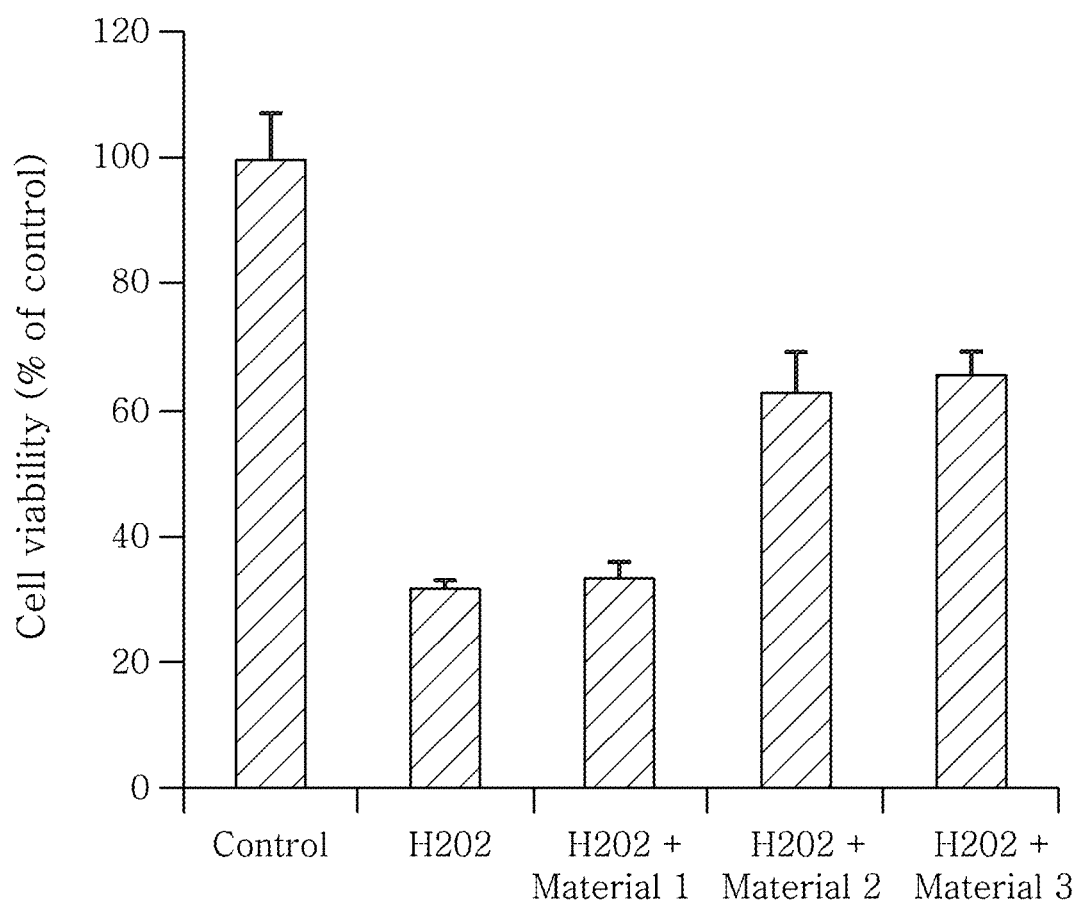
FIG. 4 shows the effects of Sample 1 to Sample 3 in terms of the effect of protecting cells from oxidative stress.

The results are shown in FIG. 4, and the cell viability in the case of using Sample 2 was higher than that in the case of using Sample 1 by two times or more. The cell viability in the case of using Sample 3 was similar to that in the case of using Sample 2. In other words, the cell viability in the case of using Sample 2 and Sample 3 was much higher than that in the case of using Sample 1.

Test Example 3: Lipid Peroxidation (MDA) Assay

Lipid peroxidation is produced by the peroxidation reaction of various kinds of biological membranes and used as a measure of oxidative stress. The lipid peroxidation (MDA) assay kit (Sigma Aldrich) was used in order to identify the effect of each sample on the amount of peroxide lipid (malondialdehyde, MDA).

Specifically, mice were orally administered with Sample 2 (100 mg/kg) or physiological saline for 4 weeks, and then administered with scopolamine (Sigma Aldrich) (3 mg/kg) or physiological saline for the last 6 days. At the last day, the brain was removed and homogenized in malondialdehyde (MDA) lysis buffer (Sigma Aldrich). The supernatant was then collected. 200 μl of the supernatant was reacted with 600 μl of TBA solution (Sigma Aldrich) at 95° C. for 1 hour, followed by cooling in an ice bath for 10 minutes. The absorbance was measured at 532 nm using a multiplate reader (Tecan). The amount of MDA was quantified by comparing the result with that of a reference sample, which was directly treated with malondialdehyde (MDA).

Figure 5:
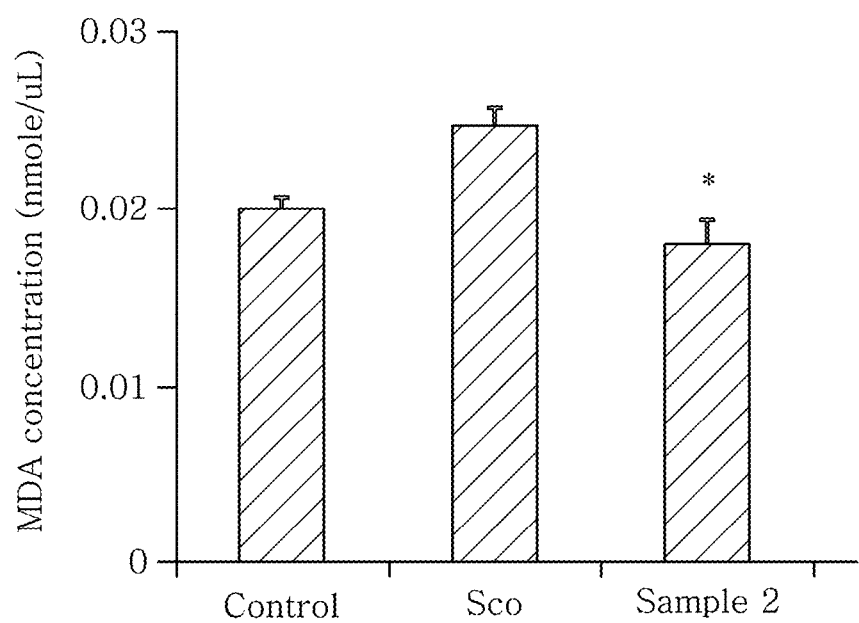
FIG. 5 shows the lipid peroxidation (MDA) assay results of Sample 2.

The results are shown in FIG. 5. From the results, it was found that the concentration of malondialdehyde (MDA) increased by the administration of scopolamine (Sco) was lowered by the intake of Sample 2 (100 mg/kg).

Test Example 4: DPPH Assay

In order to identify the antioxidative effect of samples, DPPH (diphenyl-2-picrylhydrazyl) radical scavenging ability was measured.

Specifically, Sample 1 and Sample 2 were reacted with 0.2 mM DPPH reagent (Sigma) for 30 minutes and then the absorbance of the reaction mixture was measured at 520 nm by using a spectrophotometer to examine a decrease in absorbance by reduction of DPPH. The free radical scavenging activity was determined by comparing the value of the untreated group with the value of the treated group.

DPPH scavenging ability (%)=1−(absorbance of group treated with sample/absorbance of untreated group)×100

Figure 6:
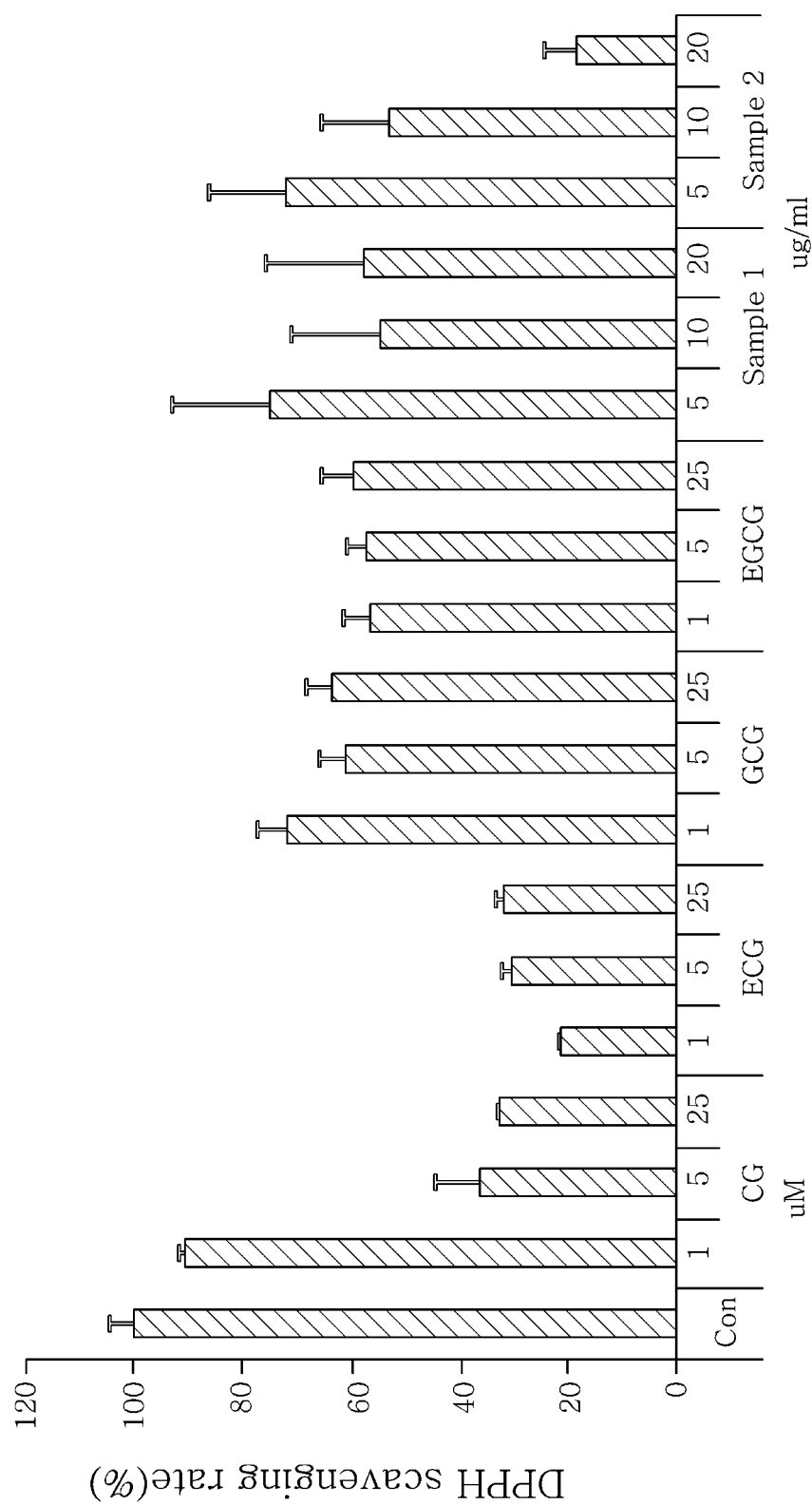
FIG. 6 shows the DPPH radical scavenging ability of Sample 1 and Sample 2.

As a result, it was found that Sample 2 exhibited much higher effect than Sample 1 at the same concentration (for example, 20 μg/ml) as shown in FIG. 6.

Formulation Example 1: Soft Capsule 150 mg of Sample 2 according to Example 1 was prepared and mixed with 440 mg of lactose, 430 mg of corn starch and 2 mg of magnesium stearate to prepare a soft capsule filling solution. Separately, a soft capsule sheet was prepared with 66 parts by weight of gelatin, 24 parts by weight of glycerin, and 10 parts by weight of sorbitol solution mand then filled with the filling solution to prepare a soft capsule.

Formulation Example 2: Tablet 150 mg of Sample 2 according to Example 1 was prepared and mixed with 15 mg of vitamin E, 15 mg of vitamin C, 250 mg of galactooligosaccharide, 60 mg of lactose, and 140 mg of maltose. The mixture was granulated using a fluidized bed dryer and then added with 8 mg of sugar ester. The resultant composition was tableted according to a conventional method to prepare a tablet.

Formulation Example 3: Drink 80 mg of Sample 2 according to Example 1 was prepared and mixed with 9 mg of vitamin E, 9 mg of vitamin C, 10 g of glucose, 0.6 g of citric acid, and 25 g of liquid oligosaccharide, followed by addition of 400 ml of purified water. The mixture was filled into a bottle and then sterilized at 30° C. for 4 to 5 seconds to prepare a drink.

Formulation Example 4: Granule 150 mg of Sample 2 according to Example 1 was prepared and mixed with 9 mg of vitamin E, 9 mg of vitamin C, 250 mg of anhydrous crystalline glucose, and 550 mg of starch. The mixture was granulated into granules using a fluidized bed granulator, which were then filled in a pouch to prepare granules.

Formulation Example 5: Health Food 150 mg of Sample 2 according to Example 1 was prepared and mixed with a mixture of vitamins (70 µg of vitamin A acetate, 1.0 mg of vitamin E, 0.13 mg of vitamin B1, 0.15 mg of vitamin B2, 0.5 mg of vitamin B6, 0.2 µg of vitamin B12, 10 mg of vitamin C, 10 µg of biotin, 1.7 mg of nicotinic acid amide, 50 µg of folic acid) and a mixture of inorganic substances (1.75 mg of ferrous sulfate, 0.82 mg of zinc oxide, 25.3 mg of magnesium carbonate, 15 mg of potassium phosphate monobasic, 55 mg of calcium phosphate dibasic, 90 mg of potassium citrate, 100 mg of calcium carbonate, 24.8 mg of magnesium chloride) to prepare a health food.

Formulation Example 6: Health Beverage 50 mg of Sample 2 according to Example 1 was prepared and mixed with 1000 mg of citric acid, 100 g of oligosaccharide, 2 g of plum concentrate, 1 g of taurine, and a balance of purified water to prepare 900 mL of a health beverage.

The extract and composition according to one aspect of the present disclosure are derived from a natural product and safe, thus protection of cells and the like from oxidative stress can be promoted. It is therefore possible to improve the quality of life of aging population without worrying about side effects and the development of related industries can be promoted.

While specific portions of the present disclosure have been described in detail, it will be apparent to those skilled in the art that these specific descriptions are merely preferred embodiments and that the scope of the present disclosure is not limited thereby. Accordingly, the actual scope of the present disclosure will be defined by the appended claims and their equivalents.

What is claimed is:

1. A method for protecting cells from oxidative stress, comprising administering a composition comprising as an active ingredient a green tea extract containing 5 to 25% by weight of (−)-gallocatechin gallate (GCG) and 7 to 15% by weight of (−)-epigallocatechin gallate (EGCG) based on the total weight of the composition to a subject in need thereof,
    wherein the total content of the GCG and EGCG in the extract is 40% by weight or less based on the total weight of the composition, and
    wherein the GCG and the EGCG are contained in the green tea extract in a weight ratio of 1:1 to 1:2.5.
2. The method according to claim 1, wherein the extract is an extract obtained by at least one extraction with at least one selected from the group consisting of water and $C_1$ to $C_4$ alcohols.
3. The method according to claim 1, wherein the content of the extract in the composition is 1 to 100% by weight on a dry weight basis.
4. The method according to claim 1, wherein the dose of the active ingredient is 5 mg/kg/day to 1000 mg/kg/day on a dry weight basis.
5. The method according to claim 1, wherein the oxidative stress results from active oxygen species.
6. The method according to claim 1, wherein the oxidative stress results from lipid peroxidation in brain tissue.
7. The method according to claim 6, wherein the oxidative stress results from the peroxidati on product malondialdehyde.
8. The method according to claim 1, wherein the cell is a brain cell or a neuron.

* * * * *